United States Patent
Mc.Neil-Watson et al.

(10) Patent No.: US 7,217,350 B2
(45) Date of Patent: May 15, 2007

(54) MOBILITY AND EFFECTS ARISING FROM SURFACE CHARGE

(75) Inventors: Fraser Keith Mc.Neil-Watson, Worcestershire (GB); Malcolm Trevor Connah, Worcestershire (GB)

(73) Assignee: Malvern Instruments Limited, Worcestershire (GB)

( * ) Notice: Subject to any disclaimer, the term of this patent is extended or adjusted under 35 U.S.C. 154(b) by 1163 days.

(21) Appl. No.: 09/843,339

(22) Filed: Apr. 26, 2001

(65) Prior Publication Data

US 2002/0040851 A1    Apr. 11, 2002

(30) Foreign Application Priority Data

Apr. 29, 2000 (GB) ................................. 0010377.0

(51) Int. Cl.
*C02F 1/469* (2006.01)
*C07K 1/26* (2006.01)
*B01D 57/02* (2006.01)
*B01D 59/42* (2006.01)

(52) U.S. Cl. ...................... 204/549; 204/601; 204/603; 204/452; 204/456; 204/451

(58) Field of Classification Search ................ 204/549, 204/601, 603, 452, 456, 451
See application file for complete search history.

(56) References Cited

U.S. PATENT DOCUMENTS 4,097,153 A * 6/1978 DeRemigis ................. 204/549
4,101,220 A * 7/1978 Bean et al. .................. 204/549
4,351,709 A * 9/1982 Goetz ......................... 204/549
5,245,290 A * 9/1993 Cannon et al. ............. 324/457

FOREIGN PATENT DOCUMENTS

WO    WO8802482 A    4/1988
WO    WO 93/04363    3/1993
WO    WO9394363 A    3/1993

* cited by examiner

*Primary Examiner*—Ling-Sui Choi
(74) *Attorney, Agent, or Firm*—Baker Botts LLP

(57) ABSTRACT

A method of, and apparatus for, automatically determining an electric charge—related characteristic or derived parameter of particles in a dispersion or of a cell wall, comprises having a particle—containing dispersion provided in a cell. The dispersion is illuminated with light from a light source and detecting from a detection volume light scattered from the particles. An electric field is applied to the dispersion at a first frequency of change of direction of the electric field and an electric field is subsequently applied to the dispersion at a second frequency of change of direction of the electric field. First signals detected from the scattered light when the first frequency electric field is applied are used to provide first values related to the velocity distribution of the particles. A second velocity related signal or value derived from scattered light during the time that the second frequency electric field is applied is used to modify the velocity distribution related values to produce a modified particle velocity-related distribution; and the first frequency is low enough to obtain an acceptable resolution of the distribution of particle velocity—related values.

9 Claims, 11 Drawing Sheets

Fig. 10B $$\text{MOBILITY } \mu = \frac{\text{VELOCITY OF PARTICLE (V)}}{\text{ELECTRIC FIELD (E)}}$$

*Fig. 11A*

$$\bar{\mu} = \frac{\int_{-\infty}^{+\infty} \mu f(\mu) d\mu}{\int_{-\infty}^{+\infty} f(\mu) d\mu}$$

WHERE $f(\mu)$ = MOBILITY SPECTRA

*Fig. 11B*

ELECTRO-OSMOTIC MOBILITY $\mu_E = \bar{\mu}_L - \bar{\mu}_H$

WHERE $\mu_L$ = PARTICLE MOBILITY AT LOW FREQUENCY APPLIED ELECTRIC FIELD.

AND $\mu_H$ = PARTICLE MOBILITY AT HIGH FREQUENCY APPLIED ELECTRIC FIELD.

WHERE $f'(\mu)$ IS THE CORRECTED FORM OF THE PARTICLE MOBILITY DISTRIBUTION FUNCTION.

MOBILITY AND EFFECTS ARISING FROM SURFACE CHARGE

This invention relates to characterising or measuring mobility and effects arising from surface charge especially but not exclusively charges on particles, or charges associated with a test cell wall. It is especially useful in the field of electrophoretic mobility, measurements, for particles using a capillary cell.

The general technique of particle electrophoresis is basically concerned with providing a suspension of fine particles or biological cells and subjecting it to a precise electric field, and hence causing the particles to attain a steady state velocity due to the charge at the surface of the particle. The surface charge may arise from ionisation of surface chemical groups or absorption of external matter, molecules or ions. Measuring this velocity can in principle allow determination of the zeta potential, which arises from the surface charge and the associated layer of ions that cluster near the surface. The velocity is often expressed as a velocity in unit electric field, which is then referred to as electrophoretic mobility.

If the surface or nature of the specimen is heterogeneous, different particles may have different charges per unit area and then the velocity will be different, and a spectrum of velocities may enable a more detailed characterisation of the specimen.

It is sometimes desired to know the electrophoretic mobility of a particle, or more likely the distribution of electrophoretic mobilities of particles. There are several prior art ways of measuring electrophoretic mobility of particles. These include direct optional observation where a user applies a DC electric field to a liquid sample that contains particles and observes them using a microscope to see how long they take to travel a given distance. From a knowledge of the velocity of the particles in the electric field and a knowledge of the strength of the electric field the electrophoretic mobility can be determined. From the mobility it is also possible to derive other useful properties of the particles, such as their zeta potential.

It is known to perform direct optical measurements of particle velocity in a bath-like sample where the electrodes are immersed directly into the liquid sample, and to perform the measurements using a capillary cell where the liquid sample dispersion is provided in a capillary (optically transparent so that the user can see the particles), and the electric field is applied axially of the capillary tube. This enables the electrodes to be provided at either end of the tube and hence kept remote from the measuring region.

The capillary also allows precise regulation of the electric field and good temperature regulation of the specimen.

The particle distribution velocity measurement is made at a certain region in the capillary cell. This is defined by the optical system. In a simple image analysis system (which is essentially a microscope) the observation consists in timing the movement of particles in a suspension in order to record the velocities of enough particles to characterise the distribution of velocities, and hence electrophoretic mobilities.

The applied field is usually periodically reversed in polarity to avoid electrode degradation and permanent loss of particles from the measuring region. The inverse of this period will be referred to as the frequency of the field.

The fluid that contains the particles will usually have ions and these ions will move under the influence of the applied electric field. The movement of the ions can effectively provide a current of liquid and the observed speed of movement of the particles dispersed in the liquid is dependent upon their charge/size and the local flow of liquid at the point where the velocity measurement is made.

In a capillary cell it is noted that at low frequencies of applied field (around 1 Hz) the velocity of the particles is dependent on the position of the point of observation It follows an apparently parabolic form in the region away from the cell walls. This is due to liquid flows set up by the effect of electric charge on the internal walls of the capillary. This flow is known as electro-osmotic flow, and its consequences are the major difficulty to overcome in exploiting the undoubted advantages of the capillary format. This is well known in the prior art. Methods used have included coating the cell walls with a neutral material and measuring at the so-called stationary layer—where the osmotic flow and counter flow cancel.

However, measuring at the stationary layer can be far from straightforward. Theoretically the stationary layer is an infinitely thin sheet, and so the best that can be achieved is to use a measurement zone which encompasses the stationary layer, and is relatively small (e.g. 50 μm inside by 50 μm tall by 50 μm deep). A major problem is aligning the optical measurement system relative to the capillary tube accurately enough, and reliably, to ensure that it is taking measurements from the correct small region at the stationary level. A small error in the alignment of the optics of the measurement device can make the results obtained unreliable, At present it can take a long time to ensure that the optics of the measurement apparatus are correctly aligned, and it can require a skilled and experienced operator to achieve proper alignment (e.g. to within 5 μm).

It is also known to use a laser beam to illuminate only a small region of the capillary, both to provide illumination for the particles and enhanced positioned selection. It is then necessary to align both the laser beam and the viewing/detector system with the same point in space and ensure that that point is at the stationary level, which is even more awkward. This requires close engineering tolerances and dust free manufacturing techniques.

The above problem has led to the development of a high frequency (e.g. ≧100 Hz) field switching technique. If the direction of the electric field is switched at high frequency it has been found that this reduces the electro-osmotic flow to a negligible amount, and so careful alignment to measure at the stationary level is no longer necessary. This technique is sometimes referred to as the Fast Field Reversal (FFR) electrophoretic mobility measurement technique.

This rapid switching can only be performed in an instrument which uses automatic methods of data collection, and the limited time for which the field is constant has a direct effect on the ability to distinguish or resolve differences in mobility.

Since in high frequency measurements particles are only observed for a short time travelling in only one direction differences in velocity distribution between the particles need to be bigger in order to be resolved: that is to say velocity differences below a threshold difference will not be resolvable or will be very difficult to resolve. Therefore the particle electrophoretic mobility distribution will be less accurately resolved (but alignment is not such a problem).

According to a first aspect the invention comprises a method of automatically determining an electric charge—related characteristic or derived parameter of particles in a dispersion or of a cell wall, comprising having a particle—containing dispersion provided in a cell; illuminating the dispersion with light from a light source; detecting from a detection volume scattered from the particles; applying an electric field to the dispersion at a first frequency of change of direction of the electric field; applying an electric field to the dispersion at a second frequency of change of direction of the electric field; using first signals detected from the scattered light when the first frequency electric field is applied to provide first values related to the velocity distribution of the particles; and using a second velocity related signal or value derived from scattered light during the time that the second frequency electric field is applied to modify the velocity distribution related values to produce a modified particle velocity—related distribution; and wherein the first frequency is low enough to obtain an acceptable resolution of the distribution of particle velocity—related values.

The second frequency is high enough that the second velocity-related signal or signals is substantially invariant on the precise position in the cell at which the detection volume is located.

The modification of the first values using the second signal value substantially compensates the first signal values for a shift in value that would otherwise be present dependant upon the position of the detection volume.

According to another aspect the invention comprises a method of determining the electrophoretic mobility of particles in a dispersion comprising having the dispersion in a capillary cell and taking particle velocity related measurements at a relatively high frequency of reversal of an applied electric field taking particle velocity measurements from the dispersion in the cell at a DC or relatively low frequency of field reversal to enable a relatively high resolution of particle velocity distribution to be obtained in comparison with the resolution that could be obtained using only measurements at the high frequency of field reversal; and using the high frequency measurements to shift the particle—velocity related distribution spectra obtained at low frequency so that the mean of its low frequency peak or peaks in the low frequency spectra substantially coincide with the position of the means of the corresponding high frequency spectral peaks, thereby producing a translated, modified, spectrum substantially equivalent to having peaks of the low frequency shape present at the positions of the equivalent high frequency peaks; and using the modified spectra to determine or indicate the electrophoretic mobility of the particles in the dispersion.

The high frequency of reversal of the electric field is such that the variation in mean velocity for a particle peak in the particle velocity distribution is substantially invariant with the precise position in the cell from which measurements are taken.

According to another aspect the invention comprises a method of determining electrophoretic values for particles in a dispersion held in a capillary, the method comprising taking particle velocity-related measurements at a high enough frequency of electric field reversal such that the effect of electro-osmotic flow of the dispersion is negligible; taking velocity—related measurements at a low enough frequency of field reversal such that electro-osmotic flow has a significant effect on the measured velocities, depending upon where in the cross-section of the capillary is the observed signal—generating region, and providing an offset to the low frequency measurements to offset the effect of the electro-osmotic flow part of the observed low frequency velocities, the offset being derived by using the high frequency measurements.

According to another aspect the invention comprises the measurement of electrophoretic mobility of a dispersion of particles or cells, the measurement being made at or near to the centre of the cross-section of a capillary cell using an optical technique that can select a sample volume that is a small fraction of the cross-section, and in which the frequency of the applied electric field is varied between high and low levels, high level being the frequency at which the electro-osmotic flow of fluid due to the electric charge on the cell wall is substantially zero at the centre of the cell and the low level being such that the parabolic flow characteristic of electro-osmosis is substantially fully established.

The particles could be biological cells.

The form of the applied field can be sinusoidal or of a square wave, or any other known shape depending on the nature of the signal processing applied.

In any preceding invention the measurement of the mean mobility of a distribution of one or more mobilities made at the high frequency may be used to adjust the spectrum of mobilities measured at the low frequency so that the mean of distribution is made identical or similar. The adjustment required may be a linear offset of the spectrum. The size and magnitude of the offset may constitute a determination of the electro-osmotic flow velocity. The adjustment could be made directly to the optics (for example by use of an optical modulator) prior to signal capture, rather than after signal capture.

It is possible to use a conversion of electrophoretic mobility and electro-osmotic velocity to provide a simultaneous determination of the zeta potential distribution of the particle dispersion and/or the zeta potential of the wall of the capillary.

Measurements may be taken at more than two electric field frequencies, possibly of the order of several, or many, (e.g ten or tens of) frequencies.

The method may comprise taking the measurements frown a detection volume that is generally on the central axis of a capillary.

The first, or low frequency may be 1 Hz±1 Hz.

The second, or high, frequency may be at least 40 Hz.

The method may comprise using the method of any preceding claim to provide parameters indicative of the electropheretic mobility and electro-osmotic velocity of the particles and dispersion, and using those parameters to determine the zeta potential distribution of the particle dispersion and/or the zeta potential of the wall of the cell.

According to another aspect the invention comprises a capillary particle electrophoretic mobility distribution determining apparatus comprising:
  a holder for a capillary cell adapted to contain a dispersion;
  a light source;
  a detector adapted to detect light scattered from a detection zone of the capillary;
  electric field generating electrodes adapted to generate an electric field;
  a controller adapted to control the electric field applied by the electrodes;
  a signal processor adapted to process the signals detected in use by the detector to determine a velocity mobility distribution; and in which
  the controller is adapted to apply an electric field at a first, relatively low, frequency and at least a second relatively high frequency, the first frequency being low enough that better velocity distribution resolution is achieved in use than could be at the second frequency, and the second frequency being high enough that the measured velocity distribution is substantially unaffected by electro-osmotic flow; and in which the processor is adapted in use to modify the particle velocity distribution spectra obtained at the first frequency by shifting it by an offset amount to remove the electro-osmotic velocity, the offset amount being determined using information from measurements at both the first and second frequencies of field reversal.

Preferably the detection zone is adapted to be substantially at the centre of the cross-section of the capillary. The light source is preferably a laser and laser doppler velocimetry is preferably used to obtain the first and/or second particle velocity distribution.

It will be appreciated that the velocity distribution is one-to-one related to the electrophoretic mobility distribution (divide by the strength of E at the measurement zone (which is known for any particular electrode voltage setting from any particular machine) to get velocity in unit field strength) and the scope of protection is intended to cover both, substantively interchangeably.

Preferably a capillary cell is present in the apparatus, but the apparatus may be sold/provided with no cell attached, the cell being obtained separately and fitted to the apparatus when full of sample.

Preferably the high frequency measurements are used to establish a mean velocity for a measured spectrum and the mean velocity of the spectrum at low velocity is used to determine the offset value (measured mean velocity of the spectrum at low frequency minus mean velocity of the spectrum at high frequency equals the electro-osmotic offset).

The first frequency may be 1 Hz ±1 Hz, or ±0.5 Hz. It may be substantially 1 Hz. The second frequency may be 100 Hz ±30 Hz, or ±15 Hz, or ±10 or ±5 Hz. Alternatively the second frequency could be significantly more than 100 Hz, for example 300, 400, 500, 600 Hz or more.

The second frequency may be at least 40 Hz.

The apparatus preferably has scattered light collecting optics and an optical alignment adjustment mechanism (or the user can preferably manually control it) to locate the detection zone to 200 μm or better, preferably to about 50 μm.

Similarly the light source preferably has a light source alignment mechanism that is manually or controller processor computer controlled to align a beam of light at the detection zone to 200 μm or better, preferably to about 50 μm. The volume of the detection zone is preferably 100 μm×100 μm×100 μm (eg. $10^6$ μm$^3$).

The controller may apply a square wave field or a sinusoidal field. The detected signals are preferably gated to ignore detected signals generated at a time close to the change of direction of movement of the particles.

The high frequency is preferably high enough to create a substantially flat parabola for the electro-osmotic flow, or at least substantially flat at the central region of the cross-section (from where the signals are detected).

The apparatus preferably has a display, printer, or output port adapted to disseminate information relating to the particle velocity distribution and/or electrophoretic mobility distribution and/or zeta potential distribution.

According to another aspect the invention comprises a data carrier embodying a computer programme which when run on a capillary electrophoretic mobility analyser performs the method of any aspect of the invention and/or creates apparatus in accordance with another aspect of the invention.

According to another aspect the invention comprises a method of determining charge-related characteristics of either (i) particles in a dispersion, or (ii) the material of a test cell wall, or (iii) particle-cell wall attraction; the method comprising providing a fluid sample having particles in it in a cell having cell walls and applying an electric field which is DC or which alternates direction at a relatively low frequency and taking DC/low frequency particle velocity measurements, and also taking particle velocity measurements when the electric field is applied at a substantially higher frequency; and using both the high frequency and low frequency measurements to determine the charge—related characteristic.

Preferably the measurements are taken from the centre of the cross-section of the cell and preferably the cell is a capillary.

We have appreciated that it is not necessary either to get good resolution at low frequency/DC but take great care to find the stationary level or to get easy to obtain/set up high frequency spectra with poorer velocity resolution, but that it is possible to use high frequency information to modify low frequency spectra to get a combined/modified high frequency spectra with alignment—insensitive set up. We have realised that at high frequency the velocity of the spectra taken at the centre of a capillary and at the stationary level are not shifted significantly as electro osmosis is negligible, and that it is possible to replace the broadened spectra with the sharper spectra from low frequency measurements.

A data carrier may embody a computer programme which when run on a capillary electrophoretic mobility analyser performs the method of any preceding aspect of the present invention and/or creates apparatus in accordance with any preceding aspect of the present invention.

According to a further aspect of the present invention there is provided a measurement cell suitable for use with a particle characterisation apparatus comprising a sample holder cell and a divider, the sample holder cell having at least a transparent portion and being arranged to hold a dispersion sample, the divider engaging a wall oil the cell and dividing a sample-holding volume of the cell and extending close to a basal face of the cell.

The divider may frictionally engage the wall of the cell.

A measurement region may be defined between the divider, which may be a dividing plate, and the basal face of the cell. A flow path, including the measurement region, may be defined between free surfaces of the dispersion on either side of the divider plate. Electrodes may be provided, possibly integrally with the cell. The electrodes may, in use, contact the dispersion. An a.c. voltage may be passed through the dispersion, in use. The cell may be used in the measurement of electrophoretic mobility distributions.

According to another aspect of the invention there is provided an electrophoretic mobility distribution sample cell having a capillary in which in use a fluid to be tested resides, in which the capillary is bent.

Preferably the capillary is U-shaped. Preferably the capillary is defined by a chamber-defining member and a divider provided in the chamber defining member so as to divide the chamber provided by the chamber-defining member to provide at least a first portion of the (capillary and at least a second portion of the capillary, the first and second portions being to opposite sides of the divider. Preferably the divider also part-defines a third portion of the capillary provided between an end of the divider and the chamber-defining member. In another embodiment the divider and the chamber-defining member define the third portion of the capillary between them, but the first and second portions of the capillary may not actually be capillary; they could be not present at all, or not necessarily narrow capillary—they could be wider sample-containing regions.

Protection is also sought for a method of providing a sample cell having a capillary, and for an automated measuring machine.

BRIEF DESCRIPTION OF THE DRAWINGS

An embodiment of the invention will now be described by way of example only with reference to the accompanying drawings of which.

Figure 1:
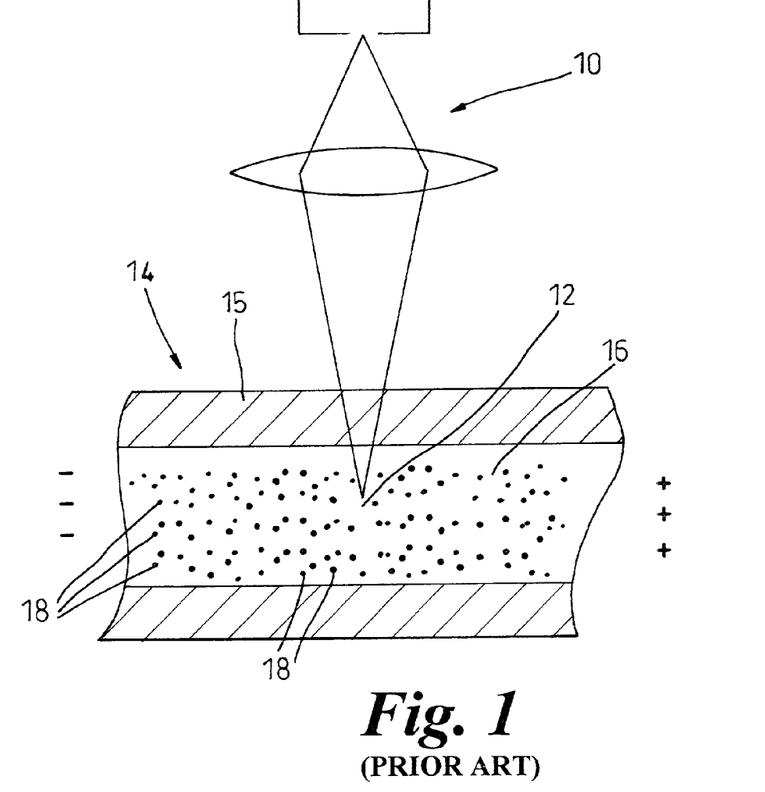
FIG. 1 illustrates schematically a prior art direct optical measurement of the velocity of particles in a capillary moving under the influence of an electric field.

FIG. 1 shows a Microscope 10 collecting light from a region 12 of a capillary test container 14. The capillary 14 has transparent walls 15 and contains a liquid 16 having a dispersion of particles 18 suspended in it. Observations are taken (e.g. normally by the eye, or with a digital camera and appropriate particle-tracking software, or with a photographic film camera and post-development processing) to determine the velocity of a number of particles, and hence determine a particle velocity distribution and/or an electrophoretic mobility distribution for the particles. The microscope 10 could, of course, be some other viewing system or optical detector.

Figure 2:
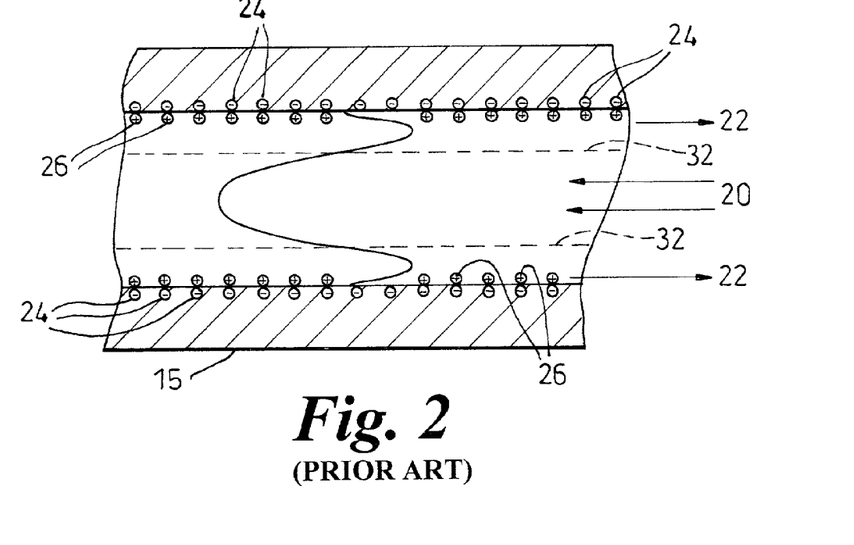
FIG. 2 illustrates schematically the phenomenon of electro-osmotic flow in a capillary and indicates the stationary level.
Figure 4:
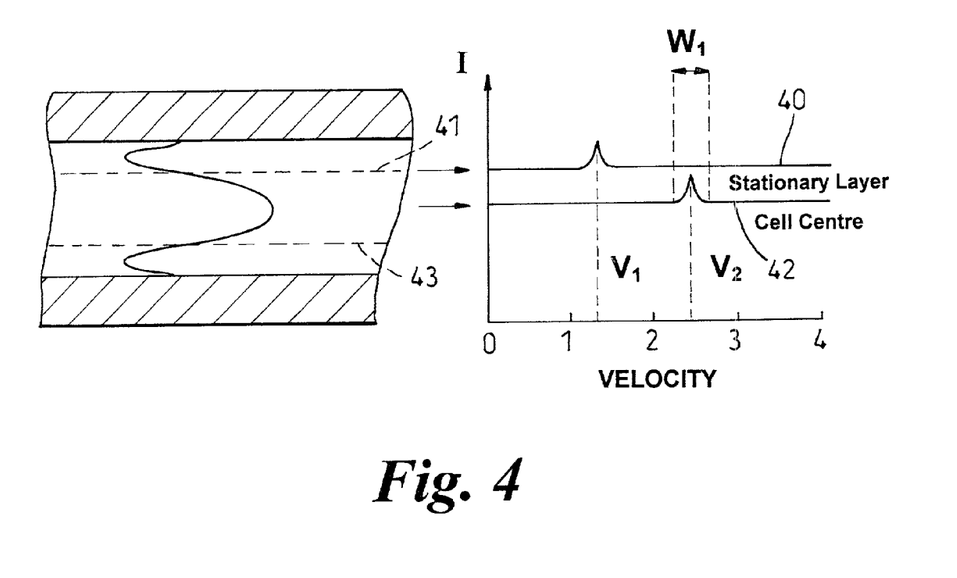
FIG. 4 illustrates the effect of measuring particle velocities at two different places in the cross-section of the capillary using a low frequency electric field.

FIG. 2 shows the phenomenon of electro-osmotic flow. This is the movement of the liquid supporting the particles dispersion due to the presence of ions, which are also transported by the electric field. The distribution of ions is affected by the charge that exists on the walls of the capillary tube and hence the net flow of liquid (and particles suspended in the liquid) depends upon distance from the wall of the capillary. The liquid flows at the periphery of the capillary in one direction, referenced 22, and at the central region of the capillary in the opposite, return, direction, referenced 20. (It has to return or else there would be a build up of liquid at one end of the cell, and the cell is full of liquid and has no space). The capillary cell wall 15 is negatively charged (reference 24) and this causes positive ions 26 to be in excess in the liquid at the inner surface of the cell wall. Line 30 of FIG. 4 illustrates the velocity of the liquid in the capillary cell. There is a tubular sheet surface, referenced 32, where the peripheral flow and the central counter flow meet and the velocity of the liquid is zero: this is the stationary level where in the prior art technique of low frequency capillary cell electrophoretic mobility measurements it is necessary to measure the particle velocity distribution (or attempt to do so). The position of the stationary layer can be calculated for simple shapes of capillary (see R. J. Hunter, Zeta Potential in Colloid Science, Academic Press 1981, p 131–134).

FIG. 4 shows a graph of normalised intensity of detected scattered light (I) against measured particle velocity for two points of measurements in the cross-sectional area of the capillary cell. The intensity of the scattered light is usually measured as photon counts per second, however it may be measured as a voltage or current which is proportional to the intensity of the scattered light. Alternatively, if image analysis is performed the intensity measurement may take the form of a particle count. Line 40 is related to measurements from the stationary layer, referenced 41, and line 42 is related to measurements from the centre of the capillary tube, referenced 43. As will be seen the detected peak when measured at the centre of the capillary is found at a different measured velocity ($V_2$) to that when measured at the level ($V_1$). This velocity shift is related to the electro-osmotic flow.

FIG. 4 shows the measurements when a low frequency electric field is applied, for example 1 Hz.

Figure 5:
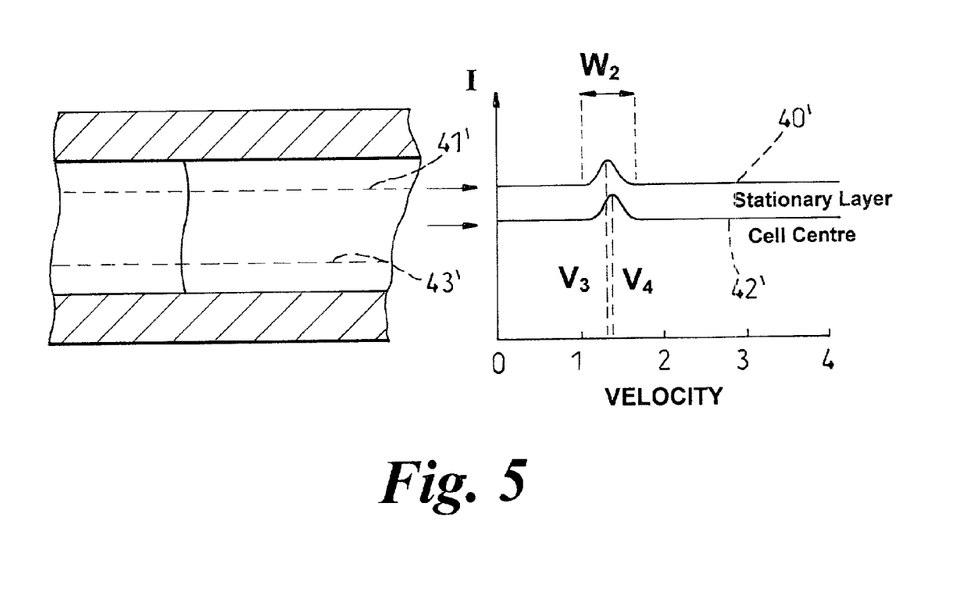
FIG. 5 illustrates the effect of measuring particle velocities at two different places in the cross-section of the capillary using a high frequency electric field.

FIG. 5 shows equivalent information to FIG. 4, but for a high frequency electric field, for example 100 Hz. Similar features have been given similar reference numbers, with the stationary layer velocity being referenced as $V_3$ and the cell centre velocity as $V_4$.

The velocities $V_1$ and $V_3$ are the velocities at the stationary layer and are relevant for establishing electrophoretic mobility. Velocities $V_2$ and $V_4$ are the velocities of particles at the centre of the cell, and are substantially the sum of the electrophoretic mobility velocity and the electro-osmotic velocity. $V_2 - V_1$ equals the liquid flow at the centre of the cell (or at any other point where $V_2$ is measured). Similarly, $V_4 - V_3$ equals the electro-osmotic flow at the point of measurement.

It will be noted that $W_1$ in FIG. 4 and $W_2$ in FIG. 5 represent the width of the velocity spectrum measured. In FIG. 4, with low frequency E, the velocity spectrum is narrow and precise information is obtained. In FIG. 5, with high frequency E, $W_2$ is broader, giving poorer resolution of the velocity of a particle/poorer resolution of a distribution of velocities of a distribution of particles.

It will be noted that in FIG. 4 the rate of change of the fluid velocity at the region of the stationary level is large (indeed the rate of change of fluid velocity with spatial position is greatest there). This means that any small error in position at which the measurement is made effects the measured value for $V_1$ significantly. On the other hands the rate of change of fluid velocity at the stationary level in FIG. 5, with high frequency, is relatively low, and the measured value of $V_3$ is relatively position-insensitive. Indeed, there is not much difference between $V_3$ and $V_4$ (and this difference is the maximum variation in measured particle velocity due to fluid flow variations). FIG. 4 has a steep parabolic curve, especially steep at just the area where it is desired to measure in the prior art low frequency technique, and FIG. 5 has an almost flat curve. This is why developments in high frequency electrophoretic mobility measurements are used. It does not matter much at about alignment of the system in high frequency measurements.

Figure 3:
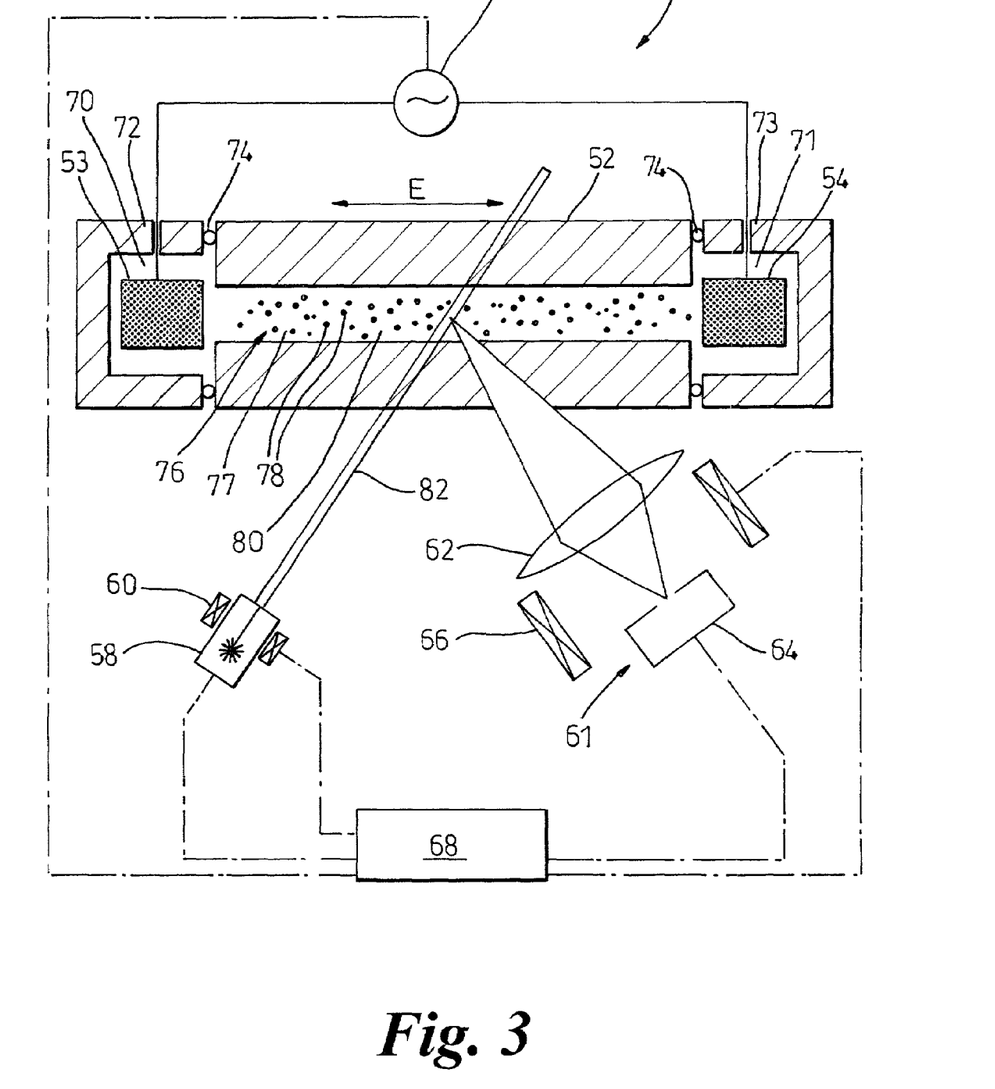
FIG. 3 illustrates schematically an instrument in accordance with the invention.

FIG. 3 shows an electrophoretic mobility measuring device or instrument 50 having a transparent capillary cell 52, a pair of electrodes 53 and 54 generating an electric field E; a power supply or voltage control system 56 controlling the voltage of the electrodes; a laser 58 and laser alignment mechanism 60; a scattered light detection system 61 comprising collection/focusing optics 62, detector 64, and detector/optics alignment mechanism 66; and control/processor 68.

The electrodes 53 and 54 are held in chambers 70 and 71 defined by chamber housings 72 and 73. Seals 74 connect the chamber housings to the cell 52 to form a closed volume for dispersion 76 which has a liquid 77 and particles 78 dispersed in the liquid.

The cell 52 is typically made of silica/quartz and is about 5 cm long by about 1 cm wide by about 1½ cm tall, and has a rectangular cross-section capillary bore 80 extending axially along its centre, the capillary hole having a cross-sectional size of about 5 mm×2 mm.

The laser alignment mechanism 60, and of the optics/detector alignment mechanism 66 are preset during manufacture to ensure that a laser beam 82 produced in use passes through (intersects) what is roughly the centre of the cross-section of the capillary bore 80, and to ensure that the optics 62 of the detection system 61 observes substantially and scattered light coming from a small volume of liquid at the centre of the capillary bore 80, where the laser beam 82 intersects the capillary (enhanced position selection). It will be appreciated that the laser beam 81 and the central optical axis of the detection system 61 may be orthogonal to each other, and orthogonal to the central axis of the capillary 52. The electric field extends along the central axis of the capillary 52.

The controller 68 controls the power supply (or voltage control system) 56 such that it produces an electric field that switches direction periodically. The controller is arranged to switch the electric field at two (or more) different frequencies. In the example of FIG. 3 the controller can select between a high field frequency (eg 100 Hz) or a low field frequency field (e.g. 1 Hz). In the preferred embodiment shown a square wave electric field of frequency between 0.5 Hz and 100 Hz is applicable to the sample.

The controller 68 also receives detected scatter signals (received from a viewing volume) from the detector 64 and analyses them to produce a particle electrophoretic mobility distribution for the sample 76 of liquid that has been introduced into the capillary 52. The detector does not image the particles, instead it uses whole field signals and monitors variations in detected intensity and looks for the doppler shifted field (doppler shift is related to velocity).

The control processor 68 effectively takes the signals representative of $V_2$ (cell centre measurement at low frequency, indicative of combined electrophoretic velocity of the particle plus electro-osmotic velocity of the liquid) and the signals representative of $V_4$ (cell centre measurement at high frequency, indicative of combined electrophoretic velocity of the particles plus electro-osmotic velocity of the liquid) and use both signals to produce a "mixed mode" value indicative: of the electrophoretic mobility dispersion of the particle, with substantially no element resulting from electro-osmotic flow.

This mixed mode, or compensated, electrophoretic mobility value is in this example achieved by subtracting the value of the centre of the $V_4$ peak, $V_4$ from the signals of the velocity distribution of particles measured at low frequency ($V_2$). This can be considered to be re-basing the zero origin of the velocity values for the low frequency measurements—introducing an offset on the velocities. The offset is what offset it takes to take the centre of the $V_2$ peak, to the value of $V_4$, which as FIG. 5 illustrates is substantially the same as $V_3$ (the stationary layer). This effect is $V_2$-$V_4$. [$V_2$-($V_2$-$V_4$)=$V_4$] It will be appreciated that $V_2$ will really be a distribution of velocities, each slightly different, and that $V_4$ will be a particular number.

Thus the instrument can be considered to take the high resolution $V_2$ peak (or more accurately, distribution of peaks resulting from different particles), which have an associated offset from the real electrophoretic velocities due to not being measured at the stationary layer, and subtracting the electro-osmotic flow contribution from their velocity by subtracting ($V_2$-$V_4$). But $V_2$ is actually a range of velocities at high resolution, and $V_4$ is to be just the single velocity that is the centre of the $V_4$ peak, so this results in a translation of the $V_2$ distribution, at high resolution, to the $V_4$ position (which is practically the same as the $V_3$, stationary layer, position).

In this way we can have good resolution of the particle velocity distribution (and have good resolution of the electrophoretic mobility distribution) by measuring in a position-insensitive way within the cross-section of the capillary. We can have the benefits of both high frequency capillary electrophoretic mobility measurements (positional errors not very significant) and the benefits of low frequency capillary electrophoretic measurements (better resolution).

It will be appreciated that although we choose to measure at the central axis of the capillary, the technique works for measurements taken anywhere in the cross-section of the capillary (although we may not wish to measure too close to the cell wall).

It will be appreciated that in our preferred embodiment we use the technique of laser doppler velocimetry in which the coherent light source produces scattered light which is mixed with a separated portion of the coherent light source to measure the velocity using the doppler technique. It is also possible to achieve a similar result using the doppler difference method in which scattered light from two beams is detected. If an incoherent light source was used we could image particles and process the images to establish its velocity.

Figure 6:
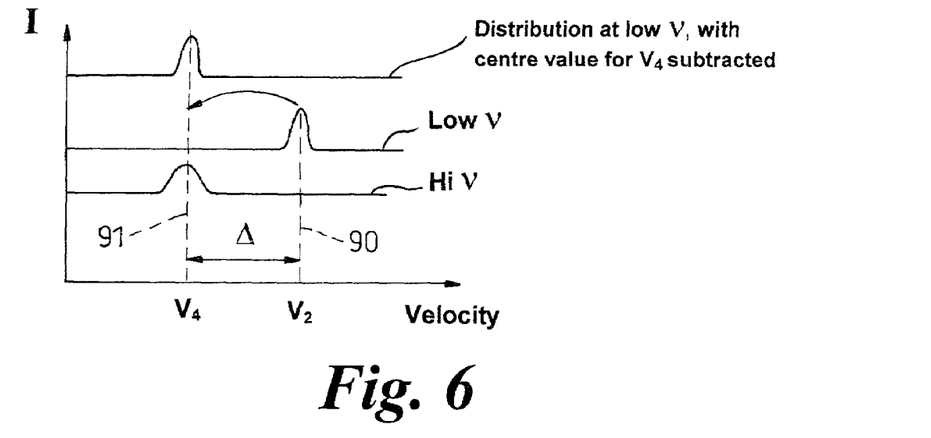
FIGS. 6 to 8 show schematically the effect of the invention.

FIG. 6 illustrates the principle of the invention. The differences $\Delta$ in velocity of the centre line 90 of the low frequency peak and the centre line 91 of the high frequency peak is closely associated with the effect that the electro-osmotic flow has on the measured velocity of the particles. This is subtracted from the low frequency velocity values to give a distribution of adjusted velocities, which is substantially the same as would be measured had the measurements been taken at the stationary level with no fluid flow.

Figure 7:
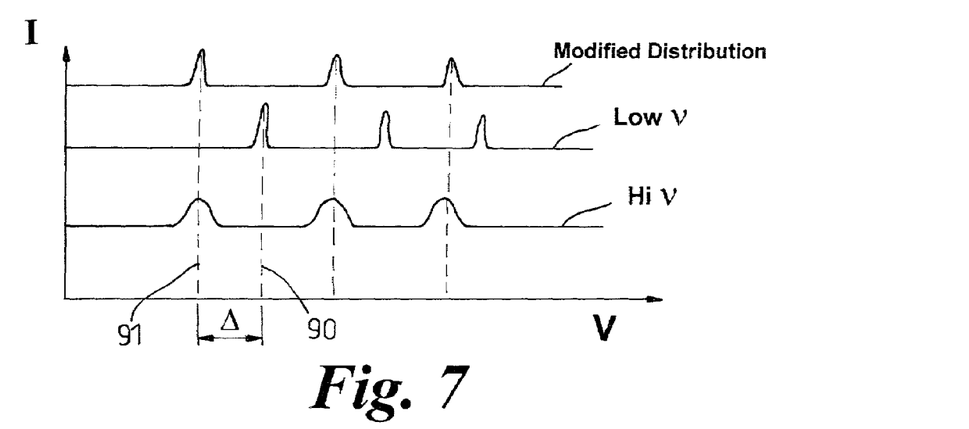

FIG. 7 illustrates a particle velocity distribution, with different particles moving at different velocities. We may evaluate $\Delta$ for one peak and subtract the same value of $\Delta$ from each low frequency velocity value, or alternatively we may recalculate $\Delta$ for each pair of matched peaks.

Figure 8:
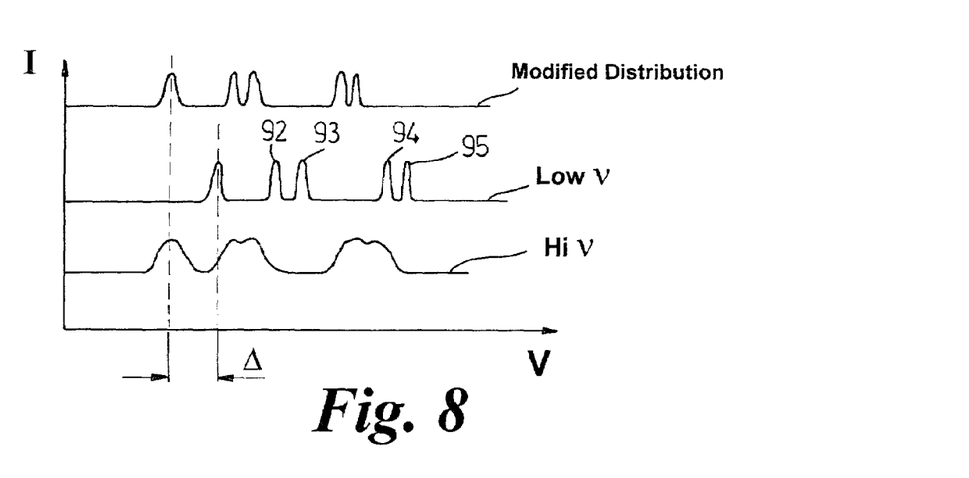

FIG. 8 shows the position where the peaks 92, 93 and 94 and 95 are so close together that at high frequency, low resolution, they cannot easily be resolved.

It will be appreciated that the relative heights of the graph lines for high v, low v, and modified distribution graph in FIGS. 6 to 8 are not to be taken as an indication of actual relative intensities—we have spread them out in I value on the graph so that they can be more easily visualised.

Figure 9:
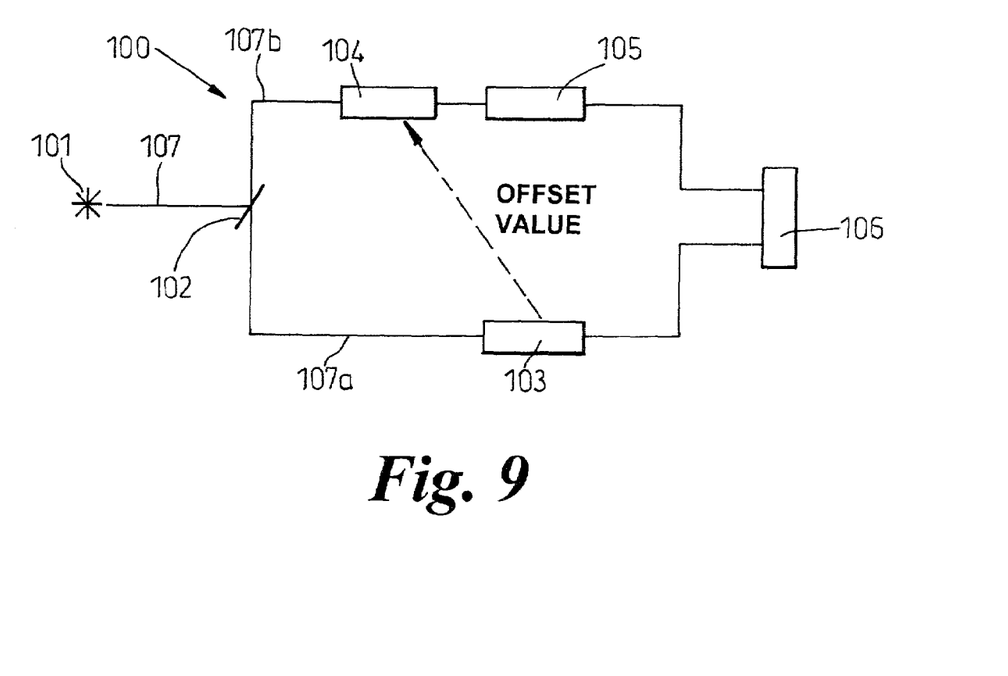
FIG. 9 shows a schematic diagram of an opto-electrical frequency offset apparatus according to the present invention.

FIG. 9 illustrates the use of the direct comparison of a measured signal which has a frequency offset imposed upon it to a reference signal prior to electronic acquisition of data from the apparatus.

The frequency adjustment apparatus 100 comprises a laser light source 101, a beam splitter 102, a reference cell 103, an optical modulator 104, a measurement cell 105 and a comparator unit 106.

The laser light source 101 emits a beam of lights 101 which is split into first and second light beam portions 107a, 107b by the beam splitter 102.

The first beam portion 107a passes through the reference cell 103 where both low and high frequency particles velocity measurements are made. The difference between the low and high frequency particle velocity measurements is stored, as an offset frequency value, and is indicative of the electro-osmotic flow characteristics of the system.

The offset frequency value is passed to the optical modulator 104.

The second beam portion 107b passes through the optical modulator 104 where it has an offset frequency equivalent to the offset frequency received from the reference cell 103 imposed upon it.

The second beam portion 107b then passes through the measurement cell 105 where high resolution, low frequency particle velocity measurements are made.

Both of the beam portions 107a, 107b are passed to the comparator unit 106 wherein a comparison between the signals can be made prior to signal capture.

It will be appreciated that in many embodiments we find only the nominal centre of the cross-section of the capillary and use the high frequency measurements to find the average peak position and the low frequency signals to provide the detail of the shape and/or height of the peak. The centre of the defined peak is used as the centre of the transposed low frequency peak (in one embodiment).

We may measure, using our apparatus, particle distributions when the particles are from 0.05 µm to 50 µm in dimension.

We believe that finding the centre of the capillary can now be done to 200±100 µm, which is far less onerous that the prior art low frequency technique where an accuracy of ±5 µm was required. The strength of our electric field is set by the electrodes and length of the capillary. The cross-section of the capillary sets the ion current flow, and hence can be used to control the heating of the sample (by ensuring a low ion flow).

Since the basis of the method is to subtract out the electro-osmotic velocity the high frequency that is used is high enough that the electro-osmotic velocity is low enough to be ignored. This will usually be at a frequency of 80 Hz or more, or 100 Hz, or 200 Hz +.

If we use too high a frequency and/or use too strong an electric field dielectrophoresis may occur, which will give erroneous results.

When the electric field is reversed the particles change direction. At the time of change of direction of movement, and around that time, the velocity of the particles is not constant (they are accelerating/decelerating). The detected signal are therefore normally gated around the transition points to ensure that the signals that are counted (those that affect the output of the calculations) are from the terminal velocity periods of movement of the particles only.

A practical target is to achieve an average of about 2%, or better, variation from the "true" velocity for a particle.

The system may use more than two frequencies for E field reversal, possibly about 3, 4, 5, 10 or more, or 20 or more.

Figure 13:
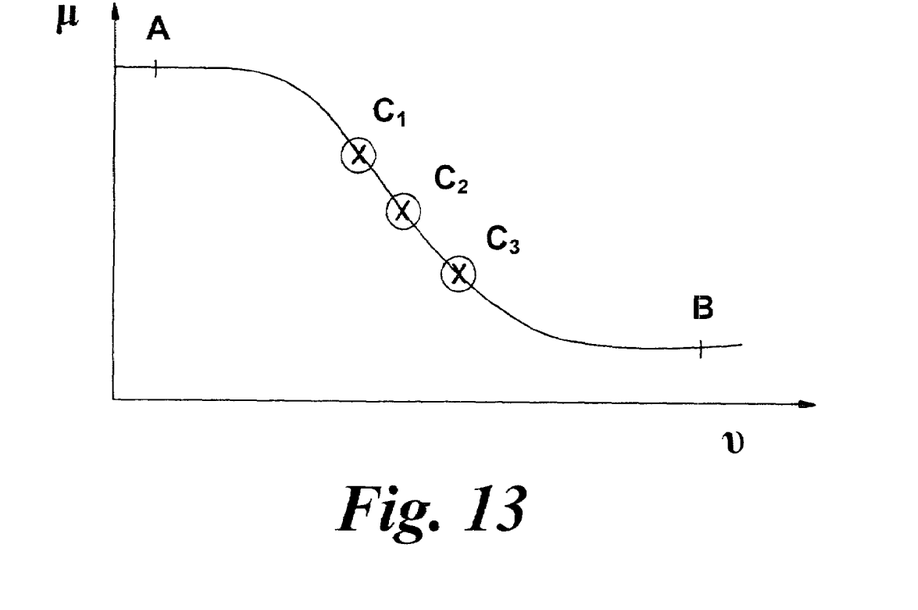
FIG. 13 shows a plot of mobility versus frequency for a particle in a specified medium.

FIG. 13 shows a typical mobility versus frequency plot for a particle whose velocity measured in an apparatus, and/or using a method, according to the present invention.

At low frequencies, typically less than 2 Hz, the electro-osmotic flow pattern is substantially parabolic between the walls of a capillary cell, and at higher frequencies, of the order of a few tens of Hz, it is effectively constant across the cell.

However, in the case of intermediate frequencies the electro-osmotic flow pattern will be a variable combination of the low and high frequency flow patterns.

Therefore, the use of a low and high frequency particle velocity measurements (points A and B respectively on FIG. 13) significantly reduces the computational complexity involved in calculating the frequency offset required to compensate for the electro-osmotic flow.

However, if the functional form of the electro-osmotic flow patterns at intermediate frequencies, is known, it may be possible to use two or more particle velocity measurements, at least one of which (or two or more) may be made at intermediate frequency values (see for example C1, C2, C3 on FIG. 13) to calculate the frequency offset.

The calculation of the frequency offset at intermediate frequency values will require the deconvolution of the electro-osmotic flow pattern from the particle velocity measurements and the extrapolation of the mobility versus frequency curve in order to obtain the low and high frequency measurements and hence the difference therebetween.

We may interleave high frequency measurements with low frequency measurements. This may help to avoid distortion of the evaluated results due to the character of the particles changing (compared to if we did several high v measurements and then several low v measurements). We may measure high v, low v pairs of measurement a number of times, say, 10 times and take an average, or integrate the signals from the high v measurements and those from the low v measurements and operate on the integrated values to determine the velocity/mobility distribution.

It is possible to measure at any point in the cross-section of the capillary for electrophoresis mobility measurements, but the measurements may also enable us to measure one or more characteristics of the cell wall. It would be better to measure generally in the middle of the capillary cross-section to obtain data indicative of all cell, wall information.

The invention combines a measurement at high frequency that measures the mean mobility of the dispersion, with a measurement at low frequency that establishes the details of the spectrum. The amount by which the latter is adjusted to predict the same mean value is a measurement of the effective state of charge of the cell wall. This is secondary, but potentially useful information.

It will be appreciated that the calculations and algorithms needed with the present invention are substantially the same as those needed with conventional laser doppler shift capillary electrophoretic mobility algorithms/calculations.

In one embodiment it is possible to simply calculate the DC or low frequency distribution shape and locate the centre of the low frequency spectrum on the centre of the high frequency spectrum (calculating both from observed scattered light data) to provide a composite result containing high resolution electrophoretic mobility spectra.

It is possible to ruse information about the charge characteristics of the cell wall to: (a) determine whether the cell wall is dirty and needs cleaning (and have the apparatus provide an automatic indication of this to the user); (b) determine the extent to which the particles in the dispersion stick/adhere to the cell wall, which can tell us additional information about the cell wall, or the particles, or both; make the cell wall out of a material in which we are interested (e.g. coat it with that material) and determine charge characteristics of the material.

Of course, it is also possible to use the velocity measurements and/or the electrophoretic mobility measurements to determine the zeta potential of the particles, and the machine may do that automatically. It may be capable of producing a display or print out of zeta potential distribution.

Although it is from the foregoing, the calculation process used by the particle electrophoretic mobility distribution analysis machine will be described, with reference to FIGS. 10 to 12.

The machine sets the amplitude of the applied electric field, either from a pre-stored programme, or the user can input it/select it. The machine then sets the frequency of the high frequency to be used (again either automatically or user selected from available options, or user input). The machine collects intensity signals at the high-frequency E field and computes the auto correlation function of the signal. The machine collects light until a required amount of light, or time, has been achieved. The process of collecting light constitutes recording successive samples integrated for, typically, 100 to 1000 microseconds, and storing these samples in a memory buffer. The conversion light to electrical signals representative of intensity may be analogue; and may use ADC converter to get digital electronic signals, or digital (in which case individual photons are counted).

An autocorrelation function is created from the stored samples and once the data collection/creation of the autocorrelation function for high frequency is complete the frequency distribution is converted to a velocity mobility distribution by performing a Fourier Transform on the correlation function and the velocity/mobility distribution is stored as a high frequency velocity/mobility distribution.

It will be appreciated that the autocorrelation function process is used to integrate the signal before later performing a Fourier Transform, but it is alternatively possible to perform the measurement directly by performing the Fourier Transform on the data directly and then integrating the F.T. results.

The machine, after establishing a particle velocity/mobility distribution at high frequency, then measures a low frequency and creates a raw low frequency particle velocity/mobility distribution.

Figure 10A:
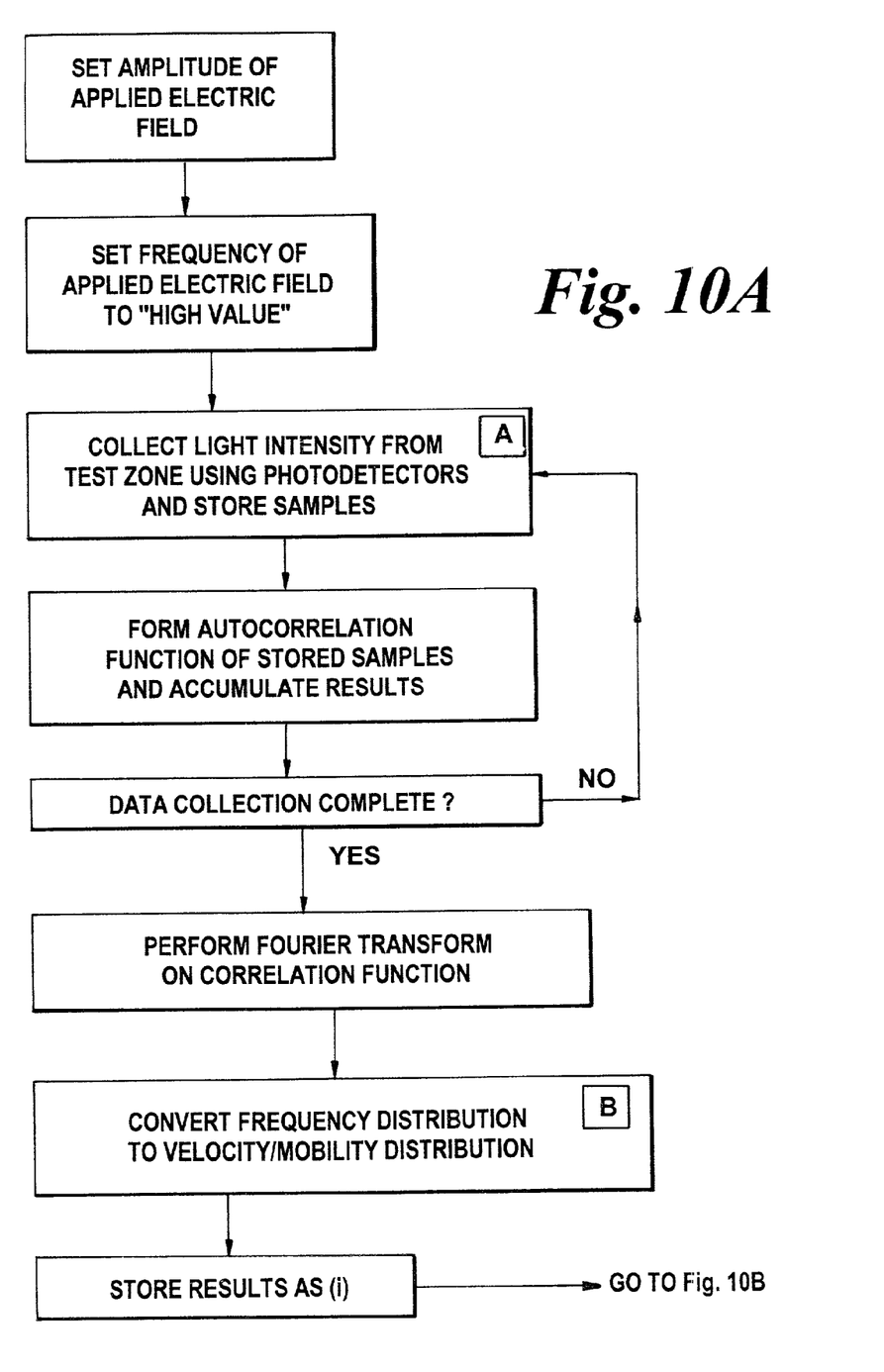
FIGS. 10A and 10B show a schematic process flow for the apparatus of FIG. 3.
Figure 10B:
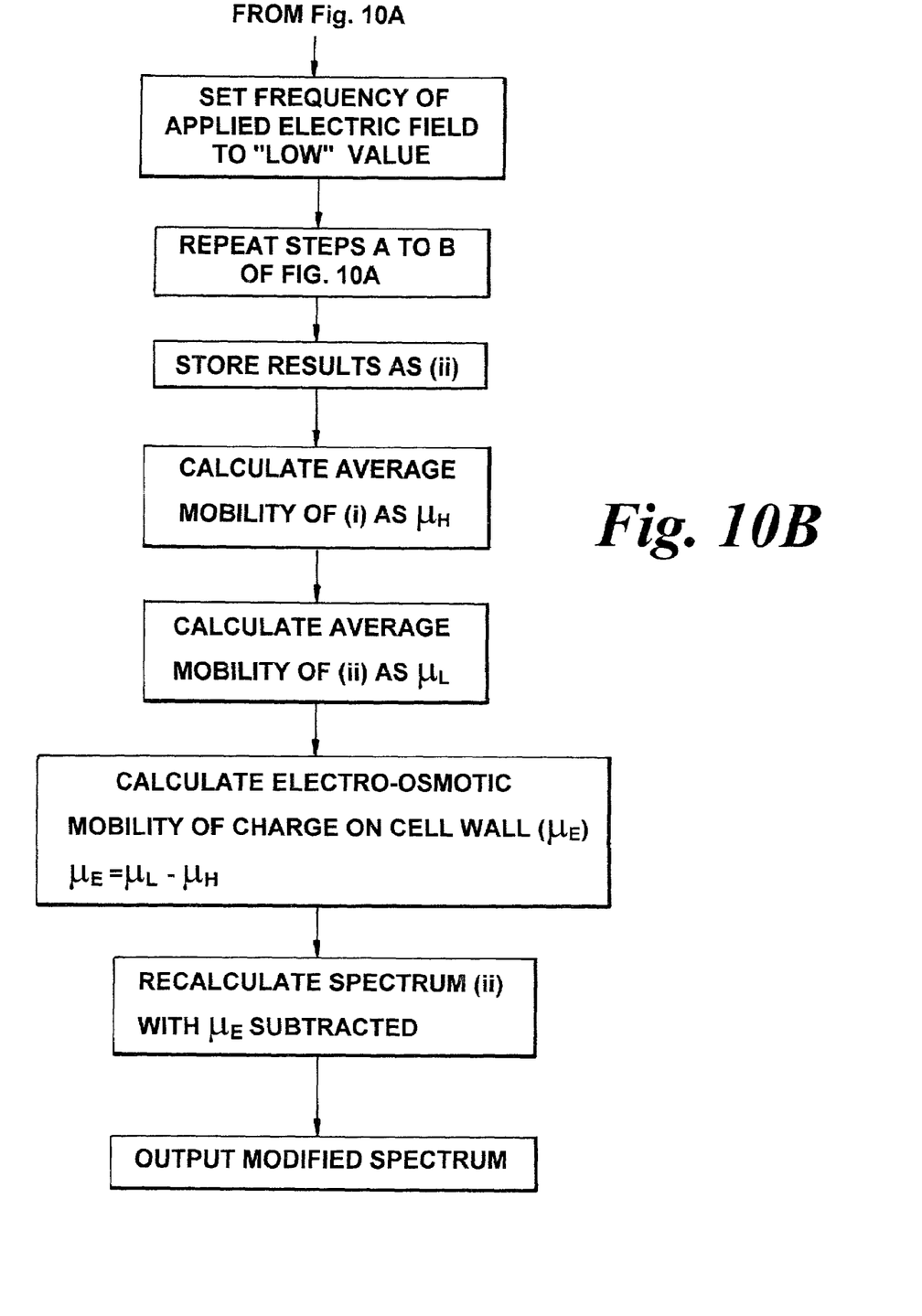
Figure 11A:
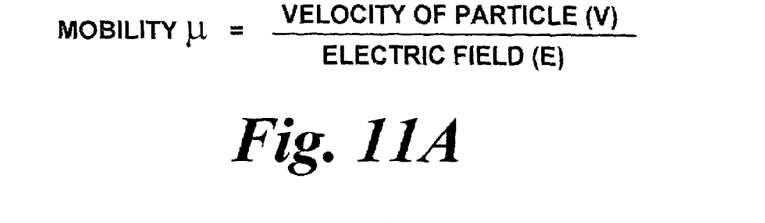
FIG. 11 shows equations used by the apparatus of FIG. 3 to produce the particle electrophoretic mobility distribution.
Figure 11B:
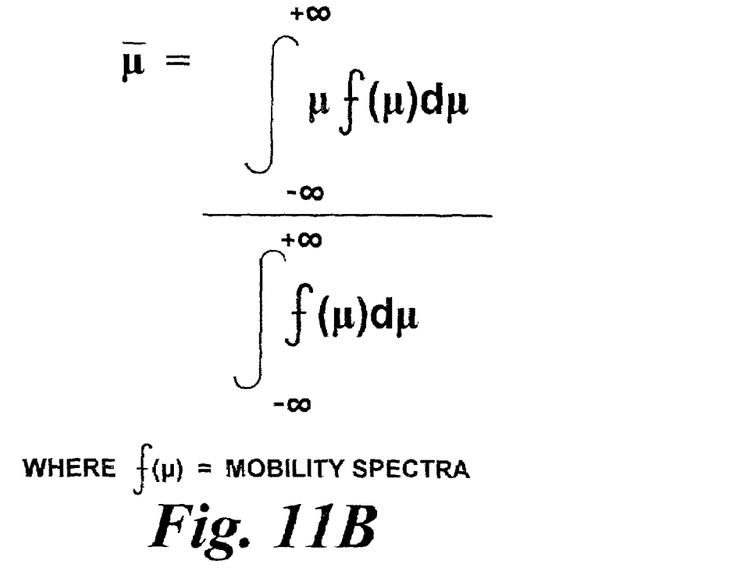
Figure 11C:
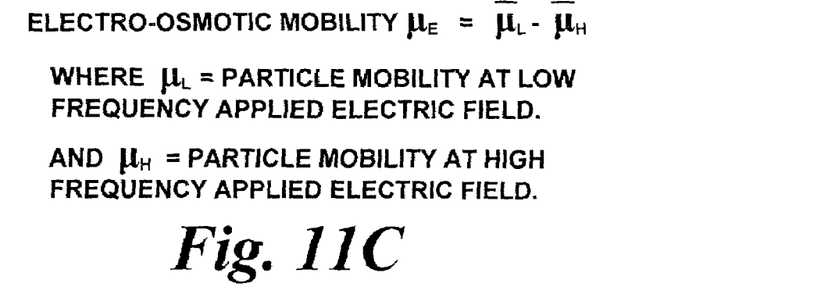
Figure 11D:
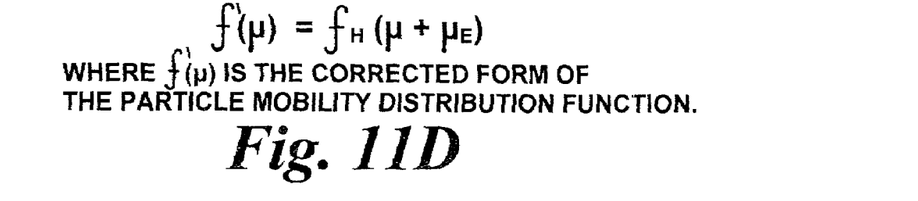

The machine then calculates a modified/corrected/particle velocity/mobility distribution in accordance with equation (d) of FIG. 10. This is then either displayed on a screen, printed out, data from it displayed or printed out, or the spectrum or data exported from the machine to some other device.

Figure 12A:
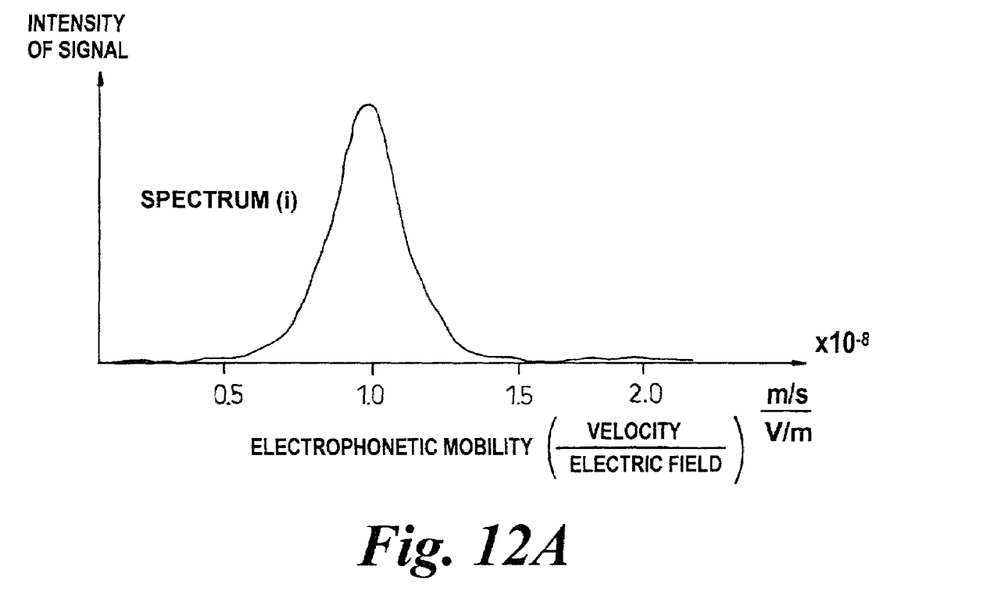
FIG. 12A and 12B show typical high frequency and low frequency particle mobility spectrum respectively.
Figure 12B:
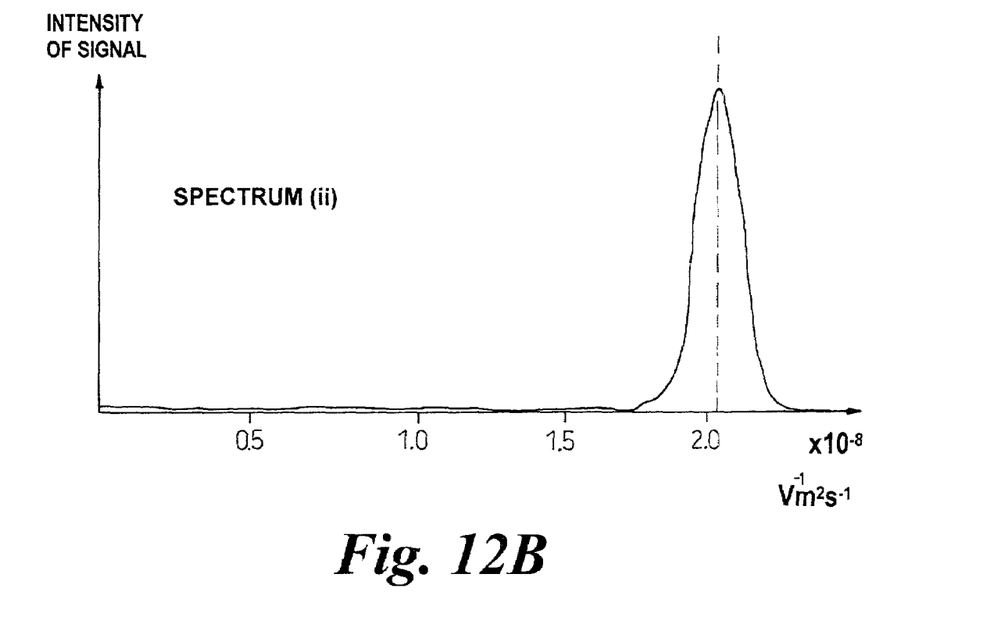

FIGS. 12A and 12B illustrate typical high and low frequency spectra measured at 100 Hz and 1 Hz respectively. It will be noted that the peak of FIG. 12B is sharper than the peak of FIG. 12A, but shifted. A low resolution method is used to evaluate the average/mean position (centre of the peak) and overlay high resolution data about that average/central peak position).

It will be appreciated that the low frequency of field reversal could be using a DC field.

Figure 14:
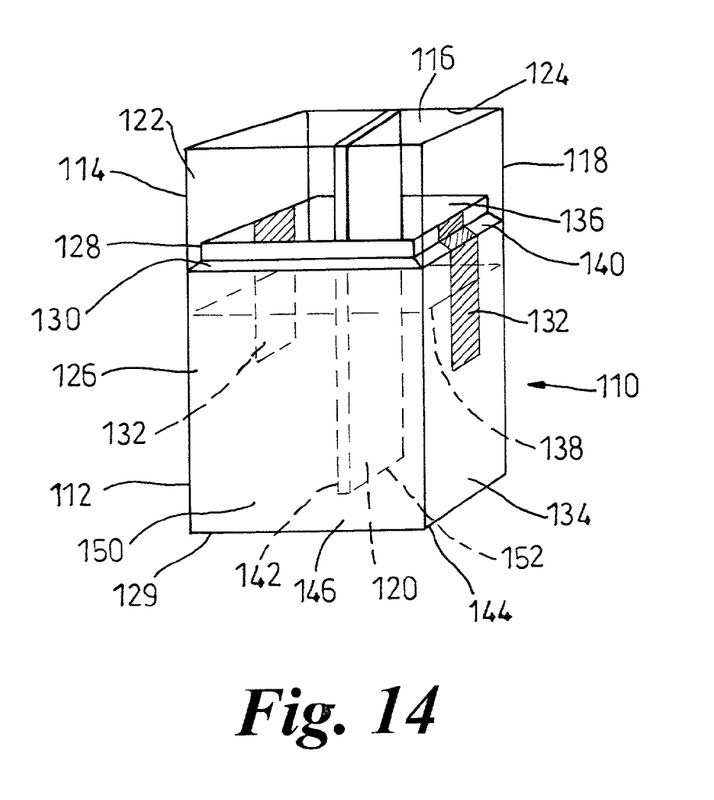
FIG. 14 is a schematic sectional view of a measurement cell suitable for use with the instrument of FIG. 3.

In a further embodiment shown in FIG. 14 a measurement cell 110 for use with the instrument of FIG. 3 comprises, a cuvette 112 of square or rectangular vertical cross-section and a cap 114.

The cap has a square end wall or face 116 with a continuous edge wall 118 projecting perpendicularly therefrom. A rectangular dividing plate 120 extends between an opposing pair of sides 122, 124 of the wall 118 and projects beyond the edge wall 118 thereof.

The cuvette 112 has side walls 126 which are inwardly stepped towards an open end 128 of the cuvette 112 so as to form a ledge 130, and a closed end 129.

A pair of opposed cuvette side walls 126 have two electrodes 132 thereupon that run from partway over an outer surfaced 134 of the walls 126, over the ledge 128 and partway over an inner surface 136 of the walls 126. The electrodes 132 are typically made of metal and are typically deposited onto the cuvette walls 126 by vacuum deposition.

In use the cuvette 112 is partially filled with a sample 138 and the cap 114 placed upon the cuvette 112 such that a free end 140 of the cap wall 118 abuts the ledge 128 and side edges 142 of the plates 120 sealingly engage inner surfaces 136 of the walls 126. The dividing plate 120 extends close to, typically within 1 mm of, a basal surface 144 of the cuvette 112 thus defining a flow path 146 between the electrodes 132, the sample 138 being in intimate contact with the electrodes 132. The flow path 146 is, in effect, a u-shaped capillary tube.

The cell 110 is placed into the instrument, either individually or mounted upon a carousel of cells. Connections are made from the a.c. supply 56 to the electrodes 132, typically by contacting conducting rods thereto. This arrangement eliminates any contact between the sample and any external contacts thereby reducing the possibility of cross-sample contamination between measurements. The mounting of multiple cells upon a carousel also allows automated multiple assays to be carried out, again due to the design of the measurement cell 110, without the concern of the cross-contaminating of samples. This is of particular interest in pharmaceutical of biotechnology applications where small volume, high cost particles are regularly measured and the cross-contamination of samples a major concern, as is a desire to use as small a volume of sample as possible.

An a.c. voltage is applied across the electrodes 132 from the supply 56 so as to cause the sample 138 to oscillate as in the measurement arrangement described hereinbefore. A measurement zone 150 is defined in the sample 138 between a free end 152 of the plate 120 and the basal surface 144 of the cuvette 112. The laser 58 is shone through the measurement zone 150 and detectors 64 are placed about the cell 112 to detect the scattered light in the conventional way. The nature of the flow path is such that precise alignment of the laser 58 through the measurement zone 150 (i.e. ±5 µm) is not necessary and an alignment accuracy of approximately 200 µm will suffice.

Figure 15:
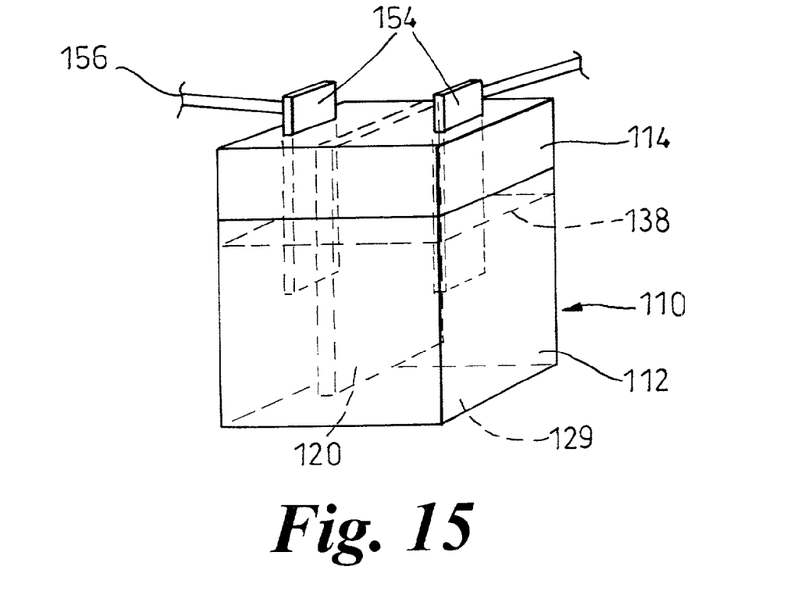
FIG. 15 is a schematic sectional view of an alternative embodiment of a measurement cell suitable for use with the instrument of FIG. 3.

In an alternative arrangement, shown in FIG. 15, conducting leaves 154 pass through the end face of the cap 114. In use when the cap is fixed on the cuvette the leaves 154 dip into the sample 138 and are connected to the a.c. power 56 supply via connectors 156. In this example the wall 120 is fixed to the cuvette, rather than being movable relative thereto.

It will be appreciated that although described as "leaves" the leaves 154 may take any convenient form, for example rods or wires.

As the cap effectively seals the open end of the cuvette resonance effects in the airspace over the sample are reduced, and the ingress of contaminants is avoided.

The measurement cell 110 requires smaller sample volumes than standard measurement cells and this is particularly advantageous where high value samples are used, for example biotechnology assays and pharmaceutical applications.

It will be appreciated that the cell can be used in conjunction with any suitable apparatus and is not limited to use with the instrument of FIG. 3.

Figure 16A:
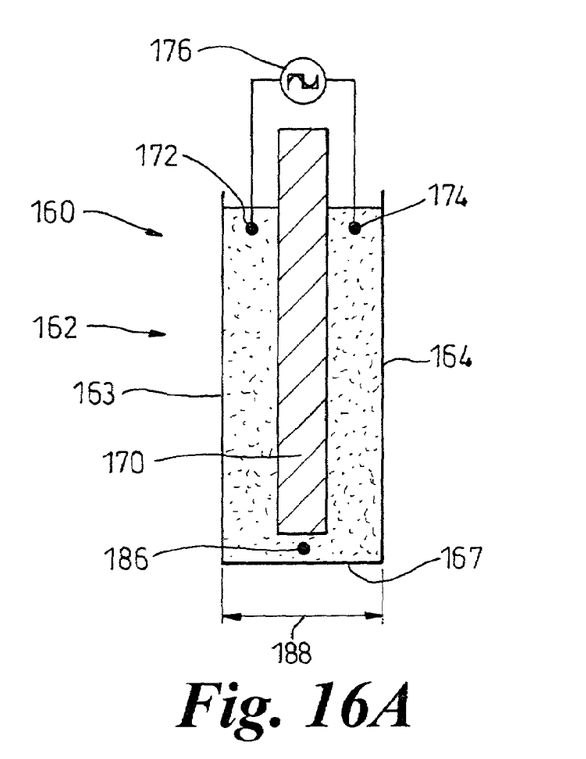
FIGS. 16A and 16B show a schematic arrangement of a measurement cell similar to that of FIGS. 14 and 15.
Figure 16B:
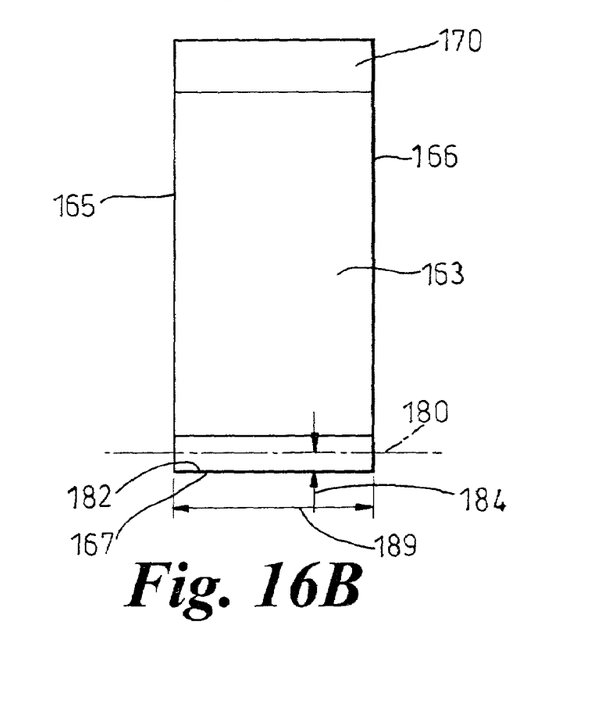

FIG. 16A shows a vertical cross-section through the measurement cell, referenced 160, shown in FIG. 16B. The cell 160 has a rectangular cuvette 162 having a front wall 163, a back wall 164, side walls 165 and 166, and a base wall 167. At least the lowermost portions, referenced 168, of the side walls 165 and 166 are transparent to the laser light of interest (all of the cuvette could be transparent). The cuvette is, for example, made of moulded plastics material. A divider 170 is disposed in the cuvette 162 in a fixed position. The divider contacts, or nearly contacts the side walls 165 and 166, and may in some embodiments seal against them. It may be a separate component to that defining the walls of the cuvette, or the walls of the cuvette and divider may be two (or more) components fixed together (for ease of moulding). Electrodes 172 and 174, and an AC power source (e.g. square wave or sinusoidal wave) 176 are provided.

In use the cuvette is filled, or partially filled with fluid to be tested (e.g. particles (solid, liquid or even gas), in a liquid (or gas)) and the AC field applied and a laser beam directed through a measurement zone at the bottom of the cell 160, between the divider 170 and the base wall 167.

FIG. 16B shows line 180 where the stationary layer of fluid is found. The distance from the internal surface, reference 182, of the wall 167 and the stationary layer 180 is references 184, and this is where the laser beam (referenced 186) should travel through the fluid. The positioning of the laser beam is not so critical as in prior art systems: ±200 μm to line 184 may be acceptable (or ±50 μm, ±100 μm, ±300 μm).

There is a different order of magnitude compared to prior art arrangements where ±5 μm is desired.

The fact that we do not need to position our beam so accurately means that we can automate the testing of samples: a machine can position the cuvette accurately enough. Also, we can use cheaper manufacturing techniques (e.g. plastics moulding) to make the cuvettes (which also do not need absolute optically flat surfaces). This means we can make cuvettes cheap enough to be disposable. Thus we could have one-shot, disposable cuvettes, which avoids problems of washing them (possibly with environmentally harmful solvents) to remove previous samples, and avoids cross-contamination problems.

An automated test apparatus, possibly with disposable cuvettes is now envisaged. The fill level of the sample in the cuvette is not critical, so long as there is enough reach the electrodes. A typical sample volume might be between 0.2 ml and 2 ml. The apparatus may have an automated test station where laser tests are carried out, a cuvette/sample holder changer to present different samples to the test station automatically, an electronic control processor, and may have a laser and scattered light detectors, and possibly a memory for storing test results. There may be an automated cuvette filler to introduce samples to cuvettes prior to testing them. The cuvette of FIGS. 16A and 16B is about 10 mm wide and 10 mm deep, shown as distances 188 and 189.

It will be appreciated that the capillary of FIGS. 16A and 16B is a bent, non-straight, capillary, with the test being performed in a straight portion of it at the U-bend of the capillary.

It will also be appreciated that our test machine can effectively have the cell loaded and removed from one side of the machine only. The cell is effectively a cartridge which can be pushed in and pulled out of an appropriate hole/slot. This enables our machine to have all, or the majority of, its user-manipulated components in the same general region of the machine (e.g. on the top). This will make it easier to use.

We claim:

1. A capillary particle electrophoretic mobility distribution determining apparatus comprising: a holder for a capillary cell adapted to contain a dispersion; a light source; a detector adapted to detect light scattered from a detection zone of the capillary; electric field generating electrodes adapted to generate an electric field in the region of the detection zone; a controller adapted to control the electric field applied by the electrodes; a signal processor adapted to process the signals detected in use by the detector to determine a velocity mobility distribution; and in which the controller is adapted to apply an electric field at a first relatively low frequency and at least a second relatively high frequency, the first frequency being low enough that better velocity distribution resolution is achieved in use than could be achieved at the second frequency, and the second frequency being high enough that the measured velocity distribution is substantially unaffected by electro-osmotic flow; and in which the processor is adapted in use to modify the particle velocity distribution spectrum obtained at the first frequency by shifting it by an offset amount to remove the electro-osmotic velocity, the offset amount being determined using information from measurements at both the first and second frequencies of field reversal.

2. Apparatus according to claim 1 in which the detection zone is adapted to be substantially at the centre of the cross-section of the capillary.

3. Apparatus according to claim 1 in which the light source is a laser and laser doppler velocimetry is used to obtain the first and/or second particle velocity distribution.

4. Apparatus according to claim 1 which comprises a capillary cell.

5. Apparatus according to claim 1 in which the high frequency measurements are, in use, used to establish a mean velocity for at least one peak and the mean velocity of the equivalent peak at low velocity is used to determine the offset value, wherein measured mean velocity particle peak at low frequency minus mean velocity of particle peak at high frequency equals the electro osmotic offset.

6. Apparatus according to claim 1 in which the first frequency is 1 Hz ±1 Hz.

7. Apparatus according to claim 1 in which the second frequency is at least 40 Hz.

8. Apparatus to claim 1 in which the controller applies a square wave field or a sinusoidal field.

9. Apparatus according to claim 1 in which the detected signals are gated to ignore detected signals generated at a time close to the change of direction of movement of the particles.

* * * * *